United States Patent [19]

Hardtmann

[11] 3,936,453

[45] Feb. 3, 1976

[54] 1-SUBSTITUTED-2-DISUBSTITUTED AMINOQUIN AZOLIN-4(1H)-ONES

[75] Inventor: Goetz E. Hardtmann, Florham Park, N.J.

[73] Assignee: Sandoz, Inc., E. Hanover, N.J.

[22] Filed: July 24, 1974

[21] Appl. No.: 491,309

Related U.S. Application Data

[63] Continuation-in-part of Ser. No. 437,472, Jan. 28, 1974, abandoned, which is a continuation-in-part of Ser. No. 373,101, June 25, 1973, abandoned.

[52] U.S. Cl... 260/256.4 Q; 260/244 A; 260/564 R; 424/251

[51] Int. Cl.[2] .......... C07D 239/84

[58] Field of Search .......... 260/256.4 Q

[56] References Cited

UNITED STATES PATENTS

| | | | |
|---|---|---|---|
| 3,149,106 | 9/1964 | Loev | 260/256.4 Q |
| 3,168,521 | 2/1965 | Wagner | 260/256.4 Q |
| 3,558,610 | 1/1971 | Breuer et al. | 260/256.4 Q |
| 3,843,654 | 10/1974 | Kirchner et al. | 260/256.4 Q |
| 3,867,384 | 2/1975 | Bullock et al. | 260/256.4 Q |

FOREIGN PATENTS OR APPLICATIONS

| | | | |
|---|---|---|---|
| 105,765 | 11/1966 | Denmark | 260/256.4 Q |

*Primary Examiner*—Nicholas S. Rizzo
*Assistant Examiner*—David E. Wheeler
*Attorney, Agent, or Firm*—Gerald D. Sharkin; Richard E. Vila

[57] ABSTRACT

Anti-histaminics of the formula

R' R $R_1$ N N $N-R_2$ $R_3$ O wherein $R_1$ is alkyl, alkenyl or phenalkyl, $R_2$ and $R_3$ are alkyl or alkenyl and R and R' are optional are prepared by alkylating or alkenylating a 1-substituted-2-monoalkyl- or alkenylamino-quinazolin-4(1H)-one with an alkyl or alkenyl halide.

10 Claims, No Drawings

1-SUBSTITUTED-2-DISUBSTITUTED AMINOQUIN AZOLIN-4(1H)-ONES

This application is a continuation-in-part of copending application Ser. No. 437,472 filed Jan. 28, 1974, now abandoned, which in turn is a continuation-in-part of copending application Ser. No. 373,101, filed June 25, 1973 now abandoned.

This invention relates to 1,2-disubstituted-quinazolin-4(1H)-ones, their preparation and the compositions and methods utilizing the pharmacological activity of said compounds.

The compounds of the invention may be represented by the structural formula I:

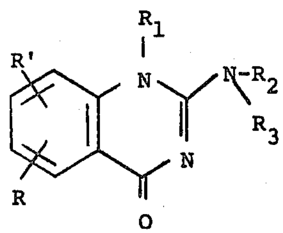

wherein $R_1$ is alkyl of 1 to 6 carbon atoms, alkenyl of 3 to 8 carbon atoms or phenalkyl of the formula II:

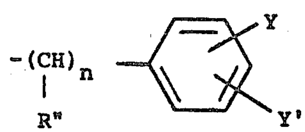

$n$ is 1 or 2

$R''$ is hydrogen or methyl provided that $R''$ is hydrogen when $n$ is 2, $R_2$ and $R_3$ are independently alkyl of 1 to 4 carbon atoms or alkenyl of 3 to 6 carbon atoms, preferably at least one of which is straight chain, and more preferably both $R_2$ and $R_3$ are straight chain, R and R' are independently hydrogen, halo of atomic weight of from 18 to 36, alkyl of 1 to 3 carbon atoms or alkoxy of 1 to 3 carbons or one is hydrogen and the other bromo or trifluoromethyl, and Y and Y'' are independently hydrogen, halo of atomic weight of from 18 to 36, alkyl of 1 to 3 carbon atoms or alkoxy of 1 to 3 carbon atoms or one is hydrogen and the other bromo or trifluoromethyl.

The compounds of the formula I may be prepared in a Step A reaction by reacting a compound of the formula II:

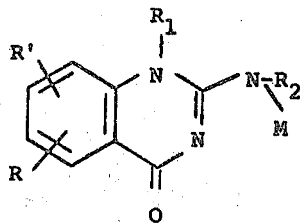

in which R, R', $R_1$ and $R_2$ are as defined and M is hydrogen or alkali metal, preferably sodium, with a compound of the formula III $$X—R_3 \qquad III$$

in which $R_3$ is as defined and X is halo of atomic weight of from 35 to 127, preferably iodo or bromo.

The reaction of Step A is of known type and preferably effected employing a compound II in which M is an alkali metal. Such compounds II may be prepared from the corresponding compound II in which M is hydrogen in a known manner with a strong base such as an alkali metal hydride or alkoxide, preferably sodium hydride. The reaction is conveniently effected at from 0°C. to 50°C., preferably at about room temperature, in an inert solvent which can be employed as solvent for the reaction of Step A. The conversion of the metallo substituted quinazolinone of the formula II to the desired product of the formula I may be carried out at temperatures of from 0°C. to 100°C., preferably 10°C. to 40°C. and conveniently at room temperature. When the Step A reaction is carried out with a compound II in which M is hydrogen, the reaction is conducted in the presence of the strong base, e.g. sodium hydride. The reaction is conducted on the basis that it may also lead to the formation of a by-product in which the 3-position of the compound of the formula II is alkylated or alkenylated. However, the desired product of the formula I may be isolated from the reaction mixture of Step A and separated from such by-product by working up by conventional procedures.

The compounds of the formula II may be prepared in a Step B by reacting a compound of the formula IV

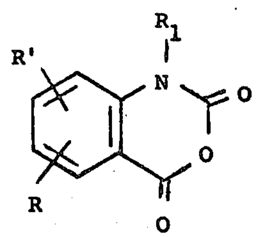

wherein $R_1$, R and R' are as above defined, with a compound of the formula V:

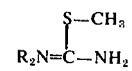

wherein $R_2$ is as defined.

The preparation of compounds II by the reaction of Step B can be carried out at temperatures in the range of 20°C. to 200°C., more usually 80°C. to 180°C., preferably 100°C. to 180°C. The reaction is conveniently carried out in an organic solvent of conventional type providing an inert reaction medium. The higher boiling solvents for use at reflux temperatures represent the preferred solvents, e.g., toluene, xylene and especially diglyme and the like. The reaction is preferably carried out in the presence of a base, e.g., potassium hydroxide, sodium hydroxide, barium hydroxide and potassium carbonate; and when the compound V is employed directly in acid addition salt form, it is of course desirable to employ an amount of base greater than the amount necessary to neutralize the acid. It will be appreciated by those skilled in the art that the compounds of the formula V are tautomeric and have the alternative and equivalent structure represented by the formula VA:

$$R_2N-\underset{|}{\overset{S-CH_3}{C}}=NR_2 \quad VA$$

wherein $R_2$ is as defined.

The compounds of the formulae IV and V are either known or may be produced from known materials by established procedures.

The compounds of formula I of the invention are useful because they possess biological activity. In particular, the compounds of the formula I are useful as agents for relieving the symptomatic effects of the release of histamine, i.e. as anti-histaminic agents, as indicated by observing the respiratory status on oral administration (1.0–100 mgs./kgs.) to the unanesthetized guinea pig exposed to aerosolized histamine dihydrochloride according to a modification of the method of Van Aman et al. J. Pharmacol. Exptl. Therap. 133: 90–97, 1961. For such use and depending upon known variables satisfactory results are obtained in general on the daily administration of from 0.5 to 100 milligrams per kilogram of body weight, preferably given in divided doses to 2 to 4 times a day, or in sustained release form. For most mammals the administration of from 40 to 1600 milligrams per day provides satisfactory results and dosage forms suitable for internal administration comprise 10 to 800 milligrams of the compound in admixture with a solid or liquid pharmaceutical carrier or diluent.

The preferred compounds of the invention from the standpoint of anti-histaminic activity are those in which $R_1$ is benzyl including substituted benzyl, particularly unsubstituted benzyl and halobenzyl, e.g., fluorobenzyl, especially 4-halobenzyl, and the more preferred compounds are those in which each of R and R' is hydrogen.

For the use indicated above, the compounds may be combined with a pharmaceutically acceptable carrier, and such other conventional adjuvants as may be necessary, and administered orally or parenterally. For most uses oral administration with carriers is preferred and may take place in such conventional forms as tablets, dispersible powders, granules, suspensions, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g, suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred pharmaceutical compositions from the standpoint of preparation and ease of oral administration are solid compositions, particularly hard-filled capsules and tablets. Parenteral administration may be in such conventional forms as injectionable solutions and suspensions.

A representative formulation is a tablet for oral administration 2 to 4 times a day for relieving the effects of histamine release and prepared by conventional tabletting techniques to contain the following ingredients:

| Ingredients | Weight (mg.) |
|---|---|
| 1-(4'-fluorobenzyl)-2-dimethylamino-quinazolin-4(1H)-one | 10 |
| Tragacanth | 10 |
| Lactose | 222.5 |
| Corn Starch | 25 |
| Talcum | 15 |
| Magnesium Stearate | 2.5 |

The following examples show representative compounds encompassed within the scope of this invention and the manner in which such compounds are prepared. However, it is to be understood that the examples are for purposes of illustration only.

EXAMPLE A 1-(4'-fluorobenzyl)-2-methylamino-quinazolin-4(1H)-one

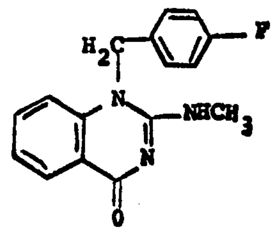

A mixture of 15 g. of N-(p-fluorobenzyl)isatoic anhydride, 15 g. of N,S-dimethylthiopseudourea (hydrogen iodide), 9.0 g. of potassium carbonate and 250 ml. of diglyme is refluxed with stirring for 1.5 hours. The resulting mixture is filtered while hot, cooled and the resulting precipitate is recovered by filtering, dissolved in methanol, dried, treated with charcoal, filtered through celite, concentrated on a steam bath and cooled to obtain a precipitate which is recovered by filtering, washed with ether and dried under reduced pressure to obtain 1-(4'-fluorobenzyl)-2-methylamino-quinazolin-2-(1H)-one, m.p. 251°–255°C.

EXAMPLE 1

1-(4'-fluorobenzyl)-2-dimethylamino-quinazolin-4(1H)-one

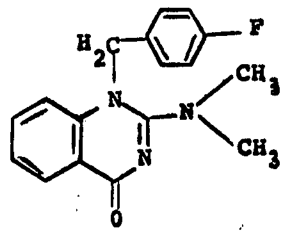

To a suspension of 0.4 g. of sodium hydride in 25 ml. of dimethylacetamide is added 2.0 g. of 1-(4'-fluorobenzyl)-2-methylamino-quinazolin-4(1H)-one. The resulting mixture is stirred for 30 minutes at room temperature and there is then added 1.5 g. of methyliodide. The resulting mixture is stirred at room temperature for 3 days, poured over ice/water, extracted twice with methylene chloride, washed twice with water, dried and evaporated in vacuo. The residue is dissolved in methylene chloride and the methylene chloride exchanged for ether on a steam bath to obtain 1-(4'-fluorobenzyl)-2-dimethylamino-quinazolin-4(1H)-one, m.p. 160°–169°C.

EXAMPLE 2

Following the procedure of Example 1, the following additional compounds of the invention are prepared.

A. 1-ethyl-2-diethylamino-quinazolin-4(1H)-one.

B. 1-(3', 4'-dimethoxybenzyl)-2-dimethylamino-quinazolin-4(1H)-one.

C. 1-(3'-trifluoromethylbenzyl)-2-dimethylamino-quinazolin-4(1H)-one.

D. 1-(4'-chlorobenzyl)-2-dimethylamino-quinazolin-4(1H)-one.

E. 7-chloro-1-benzyl-2-dimethylamino-quinazolin-4(1H)-one.

F. 6,7-dimethoxy-1-(4'-fluorobenzyl)-2-dimethylamino-quinazolin-4(1H)-one.

G. 1-(4'-fluorobenzyl)-2-N-methyl-N-allylamino-quinazolin-4(1H)-one.

EXAMPLE 3

1-(4'-fluorobenzyl)-2-allylamino-quinazolin-4(1H)-one.

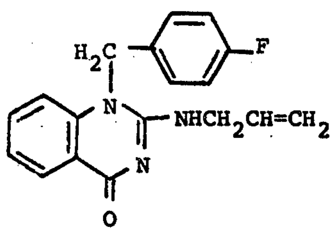

A suspension of 13.5 g. of N-(4'-fluorobenzyl)isatoic anhydride, 130 g. of S-methyl-N-allylthiopseudourea hydroiodide and 75 g. of powdered sodium carbonate in 500 ml. of acetonitrile is heated with stirring at reflux for 1.5 hours. The excess sodium carbonate is filtered off and the solvent evaporated to dryness. The residue is dissolved in methylene chloride, filtered to remove insolubles and the filtrate evaporated to dryness. The residue is dissolved in 500 ml. of diglyme and the resulting solution heated at reflux for 1.5 hours. After cooling, methylene chloride is added to obtain a precipitate which is recovered by filtering, washed twice with methylene chloride and once with ether, dried, dissolved in methanol, filtered and concentrated on a steam bath to obtain a precipitate which is recovered by filtering, washed with methanol and dried under reduced pressure to obtain 1-(4'-fluorobenzyl)-2-allylamino-quinazolin-4(1H)-one, m.p. 155°–157°C. (additional quantities of the title compound are recovered from the mother liquid).

EXAMPLE 4

Following the procedure of Example 1, the following additional compound of the invention is prepared.

A. 1-(4'-fluorobenzyl)-2-diallylamino-quinazolin-4(1H)-one.

What is claimed is:

1. A compound of the formula

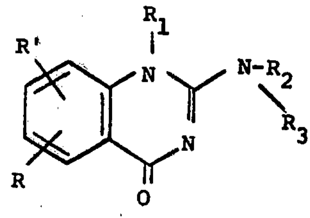

wherein $R_1$ is alkyl of 1 to 6 carbon atoms, alkenyl of 3 to 8 carbon atoms or phenalkyl of the formula:

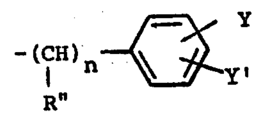

$n$ is 1 or 2

R'' is hydrogen or methyl provided that R'' is hydrogen when $n$ is 2, $R_2$ and $R_3$ are independently alkyl of 1 to 4 carbon atoms or alkenyl of 3 to 6 carbon atoms, R and R' are independently hydrogen, fluoro, chloro, alkyl of 1 to 3 carbon atoms or alkoxy of 1 to 3 carbons or one is hydrogen and the other bromo or trifluoromethyl, and Y and Y' are independently hydrogen, fluoro, chloro, alkyl of 1 to 3 carbon atoms or alkoxy of 1 to 3 carbon atoms or one is hydrogen and the other bromo or trifluoromethyl.

2. A compound of claim 1 in which $R_1$ is alkyl.

3. A compound of claim 2 in which R and R' are hydrogen.

4. A compound of claim 1 in which $R_2$ and $R_3$ are alkyl.

5. A compound of claim 1 in which each of $R_2$ and $R_3$ is methyl.

6. A compound of claim 1 in which $R_1$ is

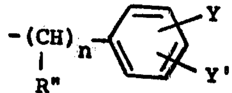

7. A compound of claim 6 in which R'' is hydrogen, $n$ is 1 and Y and Y' are selected from the group consisting of hydrogen, fluoro, chloro and bromo.

8. A compound of claim 7 in which R and R' are hydrogen.

9. A compound of claim 8 in which each of $R_2$ and $R_3$ is methyl.

10. The compound of claim 9 which is 1-(4'-fluorobenzyl)-2-dimethylamino-quinazolin-4(1H)-one.

* * * * *